United States Patent [19]

David

[11] Patent Number: 5,665,323

[45] Date of Patent: *Sep. 9, 1997

[54] PREPARATION OF AMMONIUM RARE EARTH DOUBLE OXALATES AND RARE EARTH OXIDES PRODUCED THEREFROM

[75] Inventor: Claire David, Paris, France

[73] Assignee: Rhone-Poulenc Chimie, Courbevoie Cedex, France

[*] Notice: The term of this patent shall not extend beyond the expiration date of Pat. No. 5,662,874.

[21] Appl. No.: 437,217

[22] Filed: May 8, 1995

Related U.S. Application Data

[63] Continuation of Ser. No. 131,580, Oct. 4, 1993, abandoned, which is a continuation of Ser. No. 791,206, Nov. 13, 1991, abandoned.

[30] Foreign Application Priority Data

Nov. 13, 1990 [FR] France ................................. 90 14030

[51] Int. Cl.$^6$ ................................. C01F 17/00; C07F 5/00
[52] U.S. Cl. ................................. 423/263; 534/16
[58] Field of Search ................................. 423/21.1, 263, 423/592; 534/16

[56] References Cited

U.S. PATENT DOCUMENTS

| | | | |
|---|---|---|---|
| 3,562,175 | 2/1971 | Hickok | 423/263 |
| 3,635,658 | 1/1972 | Ferri et al. | 534/16 |
| 4,238,467 | 12/1980 | Dugan et al. | 423/263 |

FOREIGN PATENT DOCUMENTS

| | | | |
|---|---|---|---|
| 748348 | 9/1970 | Belgium . | |
| 53-95911 | 8/1978 | Japan | 534/16 |
| 53-98921 | 8/1978 | Japan | 534/16 |
| 55-28905 | 2/1980 | Japan | 534/16 |
| 61-00532 | 1/1986 | Japan | 423/263 |
| 61-83143 | 4/1986 | Japan | 423/263 |
| 2205090 | 11/1988 | United Kingdom . | |

OTHER PUBLICATIONS

M.F. Barrett, et al, "Double Ammonium Oxalates of the Rare Earths and Yttrium," J. Inorg. Nucl. Chem., 1964, no month, vol. 26, pp. 931–936.

Gmelin Handbook of Inorganic Chemistry, 8th edition, 1984, no month, pp. 141–145.

Handbook of Chemistry and Physics, CRC Press, R.C. Weast, editor, 1972, pp. B–80 and B–153, no month.

Grant & Hackh's Chemical Dictionary, 5th edition, 1987, p. 496, no month.

Minagawa, et al, "New Preparative Method of Fine Powder of Yttrium (III) Oxide by Thermal Decompostion of $NH_4Y(C_2O_4)_2 \cdot H_2O$ Fine Crystal," Bull. Chem. Soc. Jpn., 63(2), Feb., 1990, pp. 378–382.

Chemical Abstracts, vol. 113, No. 6, Aug. 6, 1990, Y. Minagawa et al, "New Preparation Method of fine powder of yttrium [III] oxide by thermal decomposition of NH4Y[C2O4]2.H2O fine crystal", p. 737.

*Primary Examiner*—Steven Bos
*Attorney, Agent, or Firm*—Burns, Doane, Swecker & Mathis, L.L.P.

[57] ABSTRACT

Particulate and coarse ammonium rare earth double oxalate crystals, readily converted into rare earth oxide particles by simple calcination, e.g., yttrium oxide particles, are prepared by (a) intimately admixing, in an aqueous medium, (i) at least one rare earth neutral oxalate with (ii) at least one precursor compound adapted to liberate ammonium ions in water and (iii) at least one precursor compound adapted to liberate oxalate ions in water, (b) separating the double oxalate precipitate thus formed, and (c), optionally, washing and drying such double oxalate precipitate.

19 Claims, 1 Drawing Sheet

PREPARATION OF AMMONIUM RARE EARTH DOUBLE OXALATES AND RARE EARTH OXIDES PRODUCED THEREFROM

This application is a continuation of application Ser. No. 08/131,580, filed Oct. 4, 1993, abandoned, which is a continuation of application Ser. No. 07/791,206, filed Nov. 13, 1991, abandoned.

CROSS-REFERENCE TO COMPANION APPLICATION

My copending application Ser. No.07/791,158, now abandoned, is filed concurrently herewith and assigned to the assignee hereof.

BACKGROUND OF THE INVENTION

1. Field of the Invention

The present invention relates to the preparation of ammonium rare earth double oxalates, and to the conversion of the double oxalates thus prepared into rare earth oxides.

This invention especially relates to the preparation of such double oxalates possessing a controlled and specified morphology and particle size.

2. Description of the Prior Art

The rare earth oxides find numerous applications in such fields as, in particular, ceramics and electronics, but, at the present time, an increasing demand exists for products having controlled particle size.

One of the conventional processes for preparing rare earth oxides, and which is amply described in the literature, in particular in the *Nouveau Traits De Chimie Minerals* ("New Treatise on Inorganic Chemistry"), Volume VII, (1959), p. 1007 by Paul Pascal, entails calcining at temperatures ranging from 500° to 900° C. the rare earth oxalates prepared by precipitation, using oxalic acid, of rare earth salts in the form of an aqueous solution thereof. However, such a process produces only rare earth oxides possessing a particle size ranging from 3 to 6 µm.

It is also known to this art, per JP 53/095,911-A (Chemical Abstracts, 90, 40940 w), to prepare finely divided rare earth oxides, and more especially finely divided yttrium oxide, by calcination of an ammonium yttrium oxalate. This process comprises precipitating the yttrium in the form of its hydroxide from an aqueous solution of a yttrium salt. The aqueous solution of the yttrium salt is reacted with a basic aqueous solution such as ammonia solution, and the resulting hydroxide slurry is then treated with oxalic acid, and, finally, the resulting precipitate is separated, washed and calcined at a temperature of 750° C. According to said JP 53/095,911-A, a finely divided yttrium oxide is produced. Its particle diameter ranges from 0.9 to 4.5 µm, the crystals having the shape of small plates with rounded edges.

However, for certain applications, rare earth oxides such as yttrium oxide possessing larger particle sizes are required. Such sizes have not heretofore been attained using rare earth neutral oxalates as starting materials.

SUMMARY OF THE INVENTION

Accordingly, a major object of the present invention is the provision of a process for the preparation of ammonium rare earth double oxalates having large particle sizes, for example ranging from 5 to 10 µm.

By "ammonium rare earth double oxalate" is intended a compound comprising one or more rare earths combined with ammonium and oxalate ions and which is converted into simple or mixed oxides by calcination.

By the term "rare earths" are intended the elements of the Periodic Table having atomic numbers ranging from 57 to 71, inclusive, belonging to the lanthanide family, as well as yttrium having an atomic number of 39.

Briefly, the present invention features a process for the preparation of an ammonium rare earth double oxalate, comprising admixing, in an aqueous medium, at least one rare earth neutral oxalate with a precursor compound adapted to liberate ammonium ions and a precursor compound adapted to liberate oxalate ions in solution, separating the precipitate thus formed, and, optionally, drying said precipitate.

DETAILED DESCRIPTION OF THE PREFERRED EMBODIMENTS OF THE INVENTION

Figure 1:
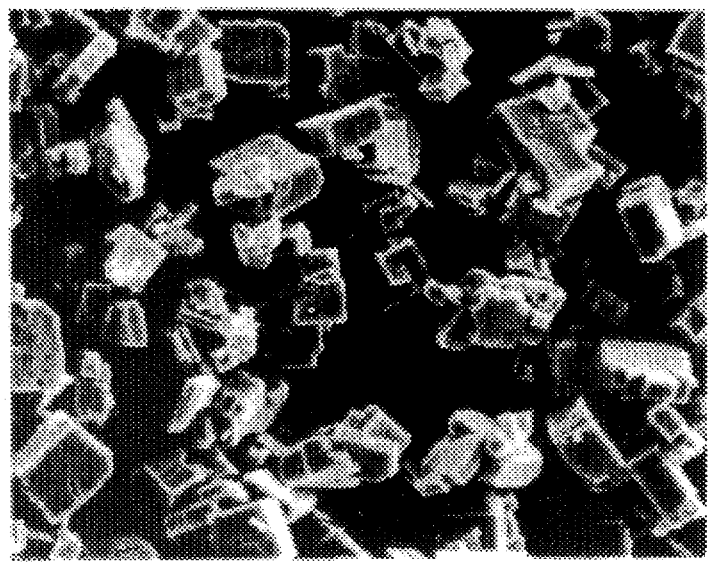
FIG. 1 is a photomicrograph (1,200X magnification) of a yttrium oxide produced by calcination of a double oxalate prepared according to the present invention.

More particularly according to the present invention, by "rare earth neutral oxalate" is intended a salt in which all of the acid functions of oxalic acid have been neutralized by a rare earth (RE) cation or cations.

According to this invention, the quantity of oxalate ions added is sufficient to provide a mole ratio of oxalate ions to rare earth ions which is advantageously not less than 2 at completion of precipitation. In effect, the yield of conversion of the neutral oxalate to a double oxalate will be higher and equal to 100% if the $C_2O_4^=/RE$ ratio is high, and in particular greater than 2.

Representative precursor compounds adapted to liberate ammonium ions in solution which are suitable for carrying out the process of the invention include all water-soluble or -insoluble compounds which liberate ammonium ions when contacted with water.

Exemplary such compounds include ammonium nitrate, ammonium chloride, ammonium acetate, ammonium hydroxide, and the like.

Similarly, representative precursor compounds adapted to liberate oxalate ions which are suitable for carrying out the process of the invention include all water-soluble or -insoluble compounds which liberate oxalate ions when contacted with water.

Exemplary such compounds include oxalic acid, crystallized or in solution, alkali metal oxalates, and the like.

In one preferred embodiment of the invention, ammonium oxalate is used as a precursor compound for the simultaneous provision of ammonium and oxalate ions. However, it is possible to use this ammonium oxalate mixed with a compound providing ammonium ions, such as ammonia, for example, or a compound providing oxalate ions, such as, for example oxalic acid.

In another embodiment of the invention, the amounts of precursor compounds adapted to liberate oxalate ions and/or ammonium ions added to the medium containing the rare earth neutral oxalate are determined such as to provide $C_2O_4^=/RE$ and $NH_4^+/RE$ mole ratios of not less than 2, and preferably not less than 2.5, upon completion of precipitation.

Exemplary rare earth neutral oxalates which are well suited for carrying out the process of the invention include yttrium, europium, lanthanum, neodymium, dysprosium, cerium, gadolinium or terbium oxalate, or mixture thereof.

Although the process of the invention applies perfectly well to the cerium rare earths, it is more especially applicable to the yttrium rare earths.

By "cerium rare earths" are intended the lighter rare earth elements beginning with lanthanum and extending up to neodymium according to atomic number, and by "yttrium rare earths" are intended the heavier rare earth elements according to atomic number, beginning with samarium and extending to lutecium, but including yttrium.

The concentration of the rare earth compound is not critical.

The rare earth neutral oxalates are prepared by all known and conventional processes such as, for example, via precipitation of the rare earth oxalate by adding oxalic acid to a solution of a soluble rare earth salt such as a rare earth nitrate.

The precursor compounds adapted to liberate oxalate or ammonium ions may be added to the medium containing the rare earth neutral oxalate in crystallized form or in the form of aqueous solutions.

These compounds may be added simultaneously or successively, rapidly or slowly, without influencing the yield of conversion of the neutral oxalate into a double oxalate. However, the rate of introduction can exert an influence on the particle size of the double oxalate, for example on the particle size distribution.

Moreover, the concentrations of $(C_2O_4)^=$ and $NH_4^+$ ions in the solutions are also not critical and can vary over wide limits.

The actual conditions for carrying out the process of the invention are essentially uncritical for producing a double oxalate. Nevertheless, control of the rate of mixing of the different solutions or the rate of introduction of the crystallized materials into the medium containing the neutral oxalate, of temperature and of the stirring of the mixture permits the morphology of the precipitated double oxalate to be modified and controlled.

Furthermore, the temperature exerts an influence on the conversion yield, since the solubility coefficient of the double oxalate and of the neutral oxalate increases with an increase in temperature.

In another preferred embodiment of the invention, the process is carried out at a temperature ranging from 50° C. to 90° C., and preferably from 60° C. to 90° C.

In yet another preferred embodiment of the invention, the separation of the precipitate is carried out between about 5 min and 2 hours after completion of precipitation. During this period, the reaction medium may be maintained under stirring or otherwise.

This step permits a rearrangement of the crystals and is generally referred to as "aging" of the precipitate.

The precipitate obtained is separated from the supernatant liquid by any solid/liquid separation process such as, for example, filtration, centrifugation, decantation or the like. It may also be subjected to one or more washings in order, for example, to remove soluble salts.

The ammonium rare earth double oxalate can be subjected to drying in order to evaporate unbound water, for example by thermal treatment at a temperature ranging from 50° C. to 100° C. or by drying under reduced pressure.

The process of the invention produces an ammonium rare earth double oxalate having a mean particle size ranging from about 5 to 10 µm, and advantageously from 7 to 10 µm. These particles are cubic in shape.

Moreover, the size of the particles of rare earth double oxalate produced is dependent on the size of the particles of neutral oxalate used, the size of the double oxalate being greater than that of the starting material neutral oxalate.

One use of these ammonium rare earth double oxalates is for the production of rare earth oxides by thermal decomposition of such oxalates.

The morphology and particle size of the rare earth oxides produced by decomposition of a double oxalate is generally similar to that of the precursor or starting material double oxalate. However, depending on the conditions of thermal treatment of the double oxalate, the particle size of the oxide may be slightly different from that of the oxalate.

Thus, the oxides produced by calcination of the double oxalates of the present invention have mean particle sizes ranging from about 5 to 10 µm, and preferably from 7 to 10 µm, with a σ/m ranging from 0.35 and 0.6.

The factor σ/m represents the particle or grain size distribution and is calculated by the following formula:

$$\frac{\sigma}{m} = \frac{\phi_{84} - \phi_{16}}{2\phi_{50}}$$

in which $\phi_{84}$ is the particle diameter for which 84% of the particles have a diameter of less than $\Phi_{84}$, $\phi_{16}$ is the particle diameter for which 16% of the particles have a diameter of less than $\Phi_{16}$ and $\phi_{50}$ is the mean particle diameter.

The thermal treatment or calcination is generally carried out at a temperature ranging from 600° C. to 1200° C., and advantageously from 800° C. to 1,000° C.

The calcination time is determined in conventional manner by monitoring for constant weight. For example, the calcination time can range from about 30 minutes to 6 hours.

In order to further illustrate the present invention and the advantages thereof, the following specific examples are given, it being understood that same are intended only as illustrative and in nowise limitative.

EXAMPLE 1

A suspension containing a yttrium neutral oxalate dried beforehand at 30° C. was heated to 85° C.

A 0.255 M solution of ammonium oxalate was added thereto to provide the following ratios of species:

$C_2O_4^-/Y=2$ $NH_4^+/Y=2$

The reaction medium was maintained under stirring for one hour.

The precipitate was recovered by filtration and washing with water, and was then dried at 100° C.

Its ammonium yttrium double oxalate structure was confirmed by X-ray analysis.

This salt was then calcined at 900° C. for one hour.

The particle size characteristics of the oxide produced were determined by analysis with a CILAS® granulometer.

The yttrium oxide possessed a mean diameter $\phi_{50}$ equal to 5.9 µm and a σ/m equal to 0.44.

EXAMPLE 2

The procedure of Example 1 was repeated, but with the following ratios of species:

$C_2O_4^-/Y=2.63$ $NH_4^+/Y=4$

The oxide obtained possessed a $\phi_{50}$ equal to 8 μm and a σ/m equal to 0.6.

The yttrium oxide produced by calcination of this double oxalate is illustrated in FIG. 1 (magnification 1,200 times).

Figure 2:
FIG. 2 is a comparative photomicrograph (1,200X magnification) of a yttrium oxide produced by calcination of a neutral oxalate.

For comparison, FIG. 2 illustrates the oxide produced by calcination of the starting neutral oxalate (magnification 1,200 times).

EXAMPLE 3

Oxalic acid was added to a suspension of yttrium neutral oxalate to provide a $C_2O_4^=/Y$ ratio equal to 2.35.

This suspension was heated to 85° C.

A 3.1 N solution of ammonia was added thereto to provide an $NH_4^+/Y$ ratio equal to 1.13.

The mixture was maintained under stirring for 30 minutes and the precipitate that formed was then filtered off and washed with water.

After drying and calcination according to the techniques described in Examples 1 and 2, the oxide obtained was analyzed with a CILAS® granulometer. It possessed a $\phi_{50}$ equal to 7 μm and a σ/m equal to 0.43.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an ammonium rare earth double oxalate, comprising (a) forming a suspension by intimately admixing, in an aqueous medium, (i) at least one rare earth neutral oxalate with (ii) at least one precursor compound liberating ammonium ions in water and (iii) at least one precursor compound liberating oxalate ions in water, and converting the rare earth neutral oxalate by precipitation into a precipitate of an ammonium rare earth double oxalate, (b) separating the double oxalate precipitate formed in step (a).

2. The process as defined by claim 1, wherein said aqueous medium the mole ratio of oxalate ions to rare earth ions is not less than 2.

3. The process as defined by claim 1, said at least one precursor compound liberating ammonium ions comprising ammonium nitrate, ammonium chloride, ammonium acetate or ammonium hydroxide.

4. The process as defined by claim 1, said at least one precursor compound liberating oxalate ions comprising oxalic acid or an alkali metal oxalate.

5. The process as defined by claim 1, wherein both said at least one precursor compound liberating ammonium ions and said at least one precursor compound capable of liberating oxalate ions comprise ammonium oxalate.

6. The process as defined by claim 1, wherein the $C_2O_4^=$/RE and $NH_4^+$/RE mole ratios upon completion of precipitation are not less than 2.

7. The process as defined by claim 6, said mole ratios being not less than 2.5.

8. The process as defined by claim 1, said at least one rare earth neutral oxalate comprising an oxalate of yttrium, europium, lanthanum, neodymium, dysprosium, cerium, gadolinium or terbium, or mixture thereof.

9. The process as defined by claim 1, said precipitation being carried out at a temperature ranging from 50° C. to 90° C.

10. The process as defined by claim 9, said precipitation being carried out at a temperature ranging from 60° C. to 90 C.

11. The process as defined by claim 1, comprising separating said double oxalate precipitate from 5 minutes to 2 hours after completion of precipitation.

12. The process as defined by claim 1, further comprising recovering particulate and coarse ammonium rare earth double oxalate crystals subsequent to step (b) and preparing a particulate and coarse rare earth oxide by calcining the particulate and coarse ammonium rare earth double oxalate crystals.

13. The process as defined by claim 12, comprising calcining at a temperature ranging from 600° C. to 1,200° C.

14. The process as defined by claim 1, further comprising a step of preparing the rare earth neutral oxalate by adding oxalic acid to a solution of a rare earth salt and precipitating the rare earth neutral oxalate.

15. A process for the preparation of an ammonium rare earth double oxalate, comprising (a) forming a suspension by intimately admixing, in an aqueous medium, (i) at least one rare earth neutral oxalate with (ii) at least one precursor compound liberating ammonium ions in water and (iii) at least one precursor compound liberating oxalate ions in water, and converting the rare earth neutral oxalate by precipitation into a precipitate of an ammonium rare earth double oxalate and (b) separating the double oxalate precipitate formed in step (a) wherein said process provides particulate and coarse ammonium rare earth double oxalate crystals having a mean particle size of at least 5 μm and cubic shape.

16. A process for preparing ammonium rare earth double oxalate crystals comprising (a) intimately admixing, in an aqueous medium, (i) at least one rare earth neutral oxalate with (ii) at least one precursor compound liberating ammonium ions in water and (iii) at least one precursor compound liberating oxalate ions in water, and converting the rare earth neutral oxalate by precipitation into crystals of an ammonium rare earth double oxalate having a mean particle size of 5–10 μm, (b) separating the double oxalate crystals thus formed, and (c) optionally, washing and drying said double oxalate crystals.

17. The process according to claim 16, further comprising calcining said crystals having a mean particle size of 5–10 μm to produce particulates of a rare earth oxide having a mean particle size of 5–10 μm and a particle size distribution of 0.35 to 0.6.

18. A process for preparing rare earth oxide particulates, wherein the double oxalate crystals of claim 16 are calcined.

19. The process according to claim 17, wherein the particulates of a rare earth oxide have a cubic shape.

* * * * *